United States Patent [19]

Sridhar et al.

[11] Patent Number: 5,756,352
[45] Date of Patent: *May 26, 1998

[54] THIOCATIONIC LIPID-NUCLEIC ACID CONJUGATES

[75] Inventors: C. Nagaraja Sridhar, Simi Valley; Jasmin R. Patel, San Diego; Nanibhushan Dattagupta, San Diego; Aditya Ranjan Das, San Diego, all of Calif.

[73] Assignee: Gen-Probe Incorporated, San Diego, Calif.

[*] Notice: The term of this patent shall not extend beyond the expiration date of Pat. No. 5,711,964.

[21] Appl. No.: 480,204

[22] Filed: Jun. 7, 1995

[51] Int. Cl.$^6$ .......................... A61K 9/127; A61K 31/70; C12N 5/10; C07H 21/04
[52] U.S. Cl. .......................... 435/375; 424/450; 514/44; 536/23.1; 935/54
[58] Field of Search .......................... 435/91.1, 172.1, 435/172.3, 240.2, 375; 514/44; 536/23.1, 24.5; 554/94, 85; 424/450; 935/54

[56] References Cited

U.S. PATENT DOCUMENTS

| | | | |
|---|---|---|---|
| 4,721,612 | 1/1988 | Janoff et al. | 424/1.21 |
| 4,886,742 | 12/1989 | Kortright et al. | 435/5 |
| 4,891,208 | 1/1990 | Janoff et al. | 424/1.21 |
| 4,897,355 | 1/1990 | Eppstein et al. | 435/172.3 |
| 5,100,662 | 3/1992 | Bolcsak et al. | 424/450 |
| 5,264,618 | 11/1993 | Felgner et al. | 560/224 |
| 5,415,869 | 5/1995 | Straubinger et al. | 424/450 |

FOREIGN PATENT DOCUMENTS

| | | |
|---|---|---|
| 0273085 | 12/1986 | European Pat. Off. . |
| 8902439 | 2/1989 | WIPO . |
| 9010448 | 9/1990 | WIPO . |
| 9116024 | 10/1991 | WIPO . |
| 9405624 | 3/1994 | WIPO . |
| 9503407 | 2/1995 | WIPO . |
| 9517373 | 6/1995 | WIPO . |

OTHER PUBLICATIONS

Gura "Antisense has growing pains" Science 270: 575–577, Oct. 1995.
Stull "Antigene, ribozyme and aptamer nucleic acid drugs: Progress and prospects" Pharm. Res. 12(4): 465–481, Apr. 1995.
Bangham, et al. Diffusion of univalent ions across the lamellae of swollen phospholipids. *J. Mol. Biol.* 13:238–252 (1965).
Behr, et al. Efficient gene transfer into mammalian primary endocrine cells with lipopolyamine–coated DNA. *Proc. Natl. Acad. Sci.* 86:6982–6986 Cell Biology (1989).
Capecchi, M. High efficiency transformation by direct microinjection of DNA into cultured mammalian cells. *Cell* 22:479–488 MIT (1980).
Cepko, et al. Construction and applications of a highly transmissible murine retrovirus shuttle vector. *Cell* 37:1053–1062 MIT (1984).

Farhood, et al. Effect of cationic cholesterol derivatives on gene transfer and protein kinase C activity. *Biochimica et Biophysica Acta*, 1111:239–246 Elsevier Science Publishers (1992).
Felgner, et al. Lipofection: a highly efficient, lipid–mediated DNA–transfection procedure. *Proc. Natl. Acad. Sci.* 84:7413–7417 Biochemistry U.S.A. (1987).
Felgner, et al. Enhanced gene delivery and mechanism studies with a novel series of cationic lipid formulations. *The Journal of Biological Chemistry* 269:2550–2561 The American Society for Biochemistry and Molecular Biology, Inc. U.S.A. (1994).
Gao and Huang. A novel cationic liposome reagent for efficient transfection of mammalian cells. *Biochemical and Biophysical Research Communications*, 197(1):280–285 Acamdeic Press, Inc. (1991).
Goodchild, et al. Conjugates of oligonucleotides and modified oligonucleotides: a review of their synthesis and properties. *Bioconjugate Chemistry* 1:165–187 American Chemical Society (1990).
Juliano, et al. Liposomes as a drug delivery system for antisense oligonucleotides. *Antisense Research and Development* 2:165–176 Mary Ann Liebert Inc. (1992).
MacKellar, et al. Synthesis and physical properties of anti–HIV antisense oligonucleotides bearing terminal lipophilic groups. *Nucleic Acids Research* 20:3411–3417 Oxford University Press (1992).
Pinnaduwage, et al. Use of a quaternary ammonium detergent in liposome mediated DNA transfection of mouse L–cells. *Biochimica et Biophysica Acta*, 985:33–37 Elsevier Science Publishers B.V. (1989).
Potter, et al. Enhancer–dependent expression of human k immunoglobulin genes introduced into mouse pre–B lymphocytes by electroporation. *Proc. Natl. Acad. Sci. U.S.A.* 81:7161–7165 (1984).
Ropert, et al. Oligonucleotides encapsulated in pH sensitive liposomes are efficient toward friend retovirus. *Biochemical and Biophysical Research Communications* 183:879–885 Academic Press, Inc. (1992).
Shea, et al. Synthesis, hybridization properties and antiviral activity of lipid–oligodeoxynucleotide conjugates. *Nucleic Acids Research* 18:3777–3783 Oxford University Press (1990).
Stamatatos, et al. Interactions of cationic lipid vesicles with negatively charged phospholipid vesicles and biological membranes. *Biochemistry* 27:3917–3925 American Chemical Society (1988).

(List continued on next page.)

*Primary Examiner*—George C. Elliott
*Assistant Examiner*—Thomas G. Larson
*Attorney, Agent, or Firm*—Charles B. Cappellari; Carlos A. Fisher

[57] ABSTRACT

Lipid molecules bearing a cationic charge are described. These cationic lipids are useful in the delivery of biomolecules, such as oligonucleotides, nucleic acids, peptides, diagnostic imaging agents, proteins and drug molecules. In the form of liposomes, they can effectively be used for the intracellular delivery of biomolecules for therapeutic or diagnostic purposes.

20 Claims, 4 Drawing Sheets

OTHER PUBLICATIONS

Stevenson, et al. Inhibition of human immunodeficiency virus type1-mediated cytopathic effects by poly(L-lysine)-conjugated synthetic antisense oligonucleotides. *J. Gen. Virol.* 70:2673–2682 SGM (1989).

Vestweber, et al. DNA-protein conjages can enter mitochondria via the protein import pathway. *Nature* 338:170–172 (1989).

Wu, et al. Receptor-mediated gene delivery and expression in vivo. *The Journal of Biological Chemistry* 263:14621–14624 The American Society for Biochemistry and Molecular Biology, Inc. U.S.A. (1988).

Zhou, et al. Lipophilic polylysines mediate efficient DNA transfection in mammalian cells. *Biochimica et Biophysica Acta.* 1065:8–14 Elsevier Science Publishers B.V. (1991).

Morris-Natshke, et al. Synthesis of phosphocholine and quaternary amine ether lipids and evaluation of in vitro antineoplastic activity. *J. Med. Chem.* 36:2018–2025 (1993).

Elgavish, et al., *In Vitro Effects of Vitamin $D_3$ On The Phospholipids Of Isolated Renal Brush Border Membranes*, J. Membrane Biol. 72:85–91, (1983).

Bennet, et al., "Cholesterol Enhances Cationic Liposome-Mediated DNA Transfection of Human Respiratory Epithelial Cells", Bioscience Reports, 15(1):47–53, (1995).

THIOCATIONIC LIPID-NUCLEIC ACID CONJUGATES

FIELD OF THE INVENTION

The present invention relates to synthetic cationic lipophilic compounds. In particular, it relates to thiocationic lipids that have a positively charged sulfonium ion, and the use of such thiocationic lipids as constituents of biomolecule conjugates and complexes, and pharmaceutical compositions thereof.

BACKGROUND OF THE INVENTION

Biomolecule-containing formulations, such as in vivo therapeutic agents, must be capable of exerting their effects on biological systems without causing toxicity and without first being degraded by normal biological processes. This sometimes requires the use of complex delivery systems and chemical modifications to make otherwise toxic and unstable compounds more efficacious. In particular, pharmaceutical agents which are highly charged, insoluble and/or high molecular weight sometimes have limited pharmacological usefulness unless they are coupled to a carrier or incorporated into a delivery vehicle.

The problems associated with successful administration of pharmaceutical formulations are compounded by the fact that certain types of pharmaceutical agents cannot exhibit their biological effects unless they are taken up by cells. For example, the use of oligonucleotides as modulators of gene function depends on their ability to interact with cellular components at the intracellular, and sometimes intranuclear, level. However, oligonucleotides, as well as other polyanionic substances, exhibit poor cellular uptake when delivered in aqueous solution.

Many different approaches have been suggested for enhancing intracellular uptake of oligonucleotides. Some involve biological approaches, such as the use of viral vectors (Cepko, et al., Cell 37: 1053–1062 (1984)), or the covalent attachment of cell receptor ligands (Myers, et al., European Patent No. 273,085 (1988); Wu et al., J. Biol. Chem., 263: 14621–14624 (1988); and Vestweber, et al., Nature 338: 170–172 (1989)). Others involve physical approaches, such as the direct microinjection of DNA into cells (Capecchi, et al., Cell 22: 479–488 (1980)) or cellular electroporation (Potter et al., Proc. Nat. Acad. Sci. 81: 7161–7165 (1984)). Yet others involve predominately chemical approaches, such as the attachment of lipophilic moieties (Shea, et al., Nucleic Acid Research 18(13): 3777–3787 (1990); MacKellar, et al., Nucleic Acid Research 20(13): 3411–3417 (1992)) or polypeptides (Stevenson, et al., J. Gen. Virol., 70: 2673–2682 (1989)).

Delivery vehicles such as liposomes have also been described for use in the intracellular delivery of oligonucleotides. (Felgner, et al., U.S. Pat. No. 5,264,618 (1993); Eppstein, et al., U.S. Pat. No. 4,897,355 (1990); and Wang, et al., Proc. Nat. Acad. Sci. 84: 7851–7855 (1987)). An advantage of using liposome formulations is the ability of these substances to mimic naturally occurring cellular membrane substituents. This encourages fusion with cellular and endosomal membranes, which results in delivery of the liposome contents into the cytoplasm. Without such membrane fusion, extracellular substances are taken up by endocytosis and may be degraded within phagosomes before being released into the cytoplasm.

Liposomes which are most useful for the intracellular delivery of biomolecules are often complex formulations containing mixtures of different lipophilic substituents. These complex mixtures allow for optimization of the physical properties of the liposomes, such as pH sensitivity, temperature sensitivity and size. One recent advance is in the recognition that certain pH sensitive amphiphilic compounds, such as dioleoylphosphatidylethanolamine ("DOPE"), can be used to formulate liposomes which destabilize at acidic pH. This promotes fusion of the liposome with endosomal membranes when exposed to the degradative acidic pH and enzymatic contents of the endosome, which results in release of the contents of the lysosome into the cytoplasm. (See Ropert, et al., Biochem. Biophys. Res. Comm. 183(2): 879–895 (1992); and Juliano, et al., Antisense Research and Development 2: 165–176 (1992)).

The inclusion of sterols in liposomes is also commonplace. In general, the presence of sterols in liposome formulations results in enhanced stability, both in vitro and in vivo. Liposome formulations for the delivery of biomolecules which contain organic acid derivatives of sterols, such as cholesterol or vitamin $D_3$, have been reported to be easier to formulate than their non-derivatized water-insoluble equivalents (Janoff, et al. U.S. Pat. Nos. 4,721,612 and 4,891,208). However, in complex liposomal formulations containing certain polar lipids, the inclusion of such water soluble acid sterol derivatives may destabilize liposomes and thus diminish efficacy.

Cationic lipids (i.e. derivatives of glycerolipids with a positively charged ammonium or sulfonium ion-containing headgroup) are particularly useful in liposomal formulations for the intracellular delivery of negatively charged biomolecules, such as oligonucleotides. Their usefulness may be derived from the ability of their positively charged headgroups to interact with negatively charged cell surfaces. The cationic lipid N-[1-(2,3-dioleyloxy)propyl]-N,N,N-trimethylammonium chloride ("DOTMA") is described by Felgner et al. (Proc. Nat. Acad. Sci. 84: 7413–7417 (1987); see also U.S. Pat. No. 4,897,355). Therein, a cationic lipid having an ammonium group is used in a liposome formulation to facilitate transfection of cells by polynucleotides. In these formulations, DOTMA has been shown to spontaneously interact with DNA to form ionic lipid-DNA complexes that are capable of fusing to negatively charged lipids on cell surfaces, ultimately leading to the uptake of DNA by the cell.

Several other ammonium ion-containing cationic lipid formulations have also been reported for such applications. These formulations include a DOTMA analog, 1,2-bis (oleoyloxy)-3-trimethylammonio)propane ("DOTAP") (Stamatatos et al., Biochemistry, 27: 3917–3925 (1988)); a lipophilic derivative of spermine (Behr et al., Proc. Nat. Acad. Sci., 86: 6982–6986 (1989)); and cetyltrimethylammonium bromide (Pinnaduwage et al., Biochim. Biophys. Acta, 985: 33–37 (1989)) (See also Leventis et al., Biochim. Biophys. Acta, 1023: 124–132 (1990); Zhou et al., Biochim. Biophys. Acta, 1065: 8–14 (1991); Farhood et al., Biochim. Biophys. Acta, 1111: 239–246 (1992); and Gao, et al., Biochem. Biophys. Res. Commun., 179: 280–285 (1991)). Some commercially available cationic lipids include DOTMA (Gibco BRL, Bethesda, Md.), DOTAP (Boehringer Mannheim, Germany), and 1,2-diacyl-3-trimethylammonium propane ("TAP") (Avanti Polar Lipids, Birmingham, Ala.). However, many of these ammonium ion-containing lipids have been reported to be cytotoxic.

Sulfonium ions have entirely different physical properties than ammonium ions. In fact, ammonium ion-containing compounds are classified as hard bases, because the nitrogen atom possesses high electronegativity, is hard to polarize and oxidize, and the valence electrons are held tightly by the nucleus. This characteristic may account for some of the toxicity associated with ammonium ion-containing lipid formulations. In contrast, sulfonium ion-containing compounds are classified as soft bases, because the sulfur atom possesses low electronegativity, is easy to polarize and oxidize, and the valence electrons are held more loosely by the nucleus. This decreased charge density exhibited by sulfonium ion-containing (i.e. "thiocationic") lipids may effectuate an enhanced interaction with negatively charged cellular membranes, as well as a decreased toxicity.

It has also been suggested that one important feature which is associated with the usefulness of lipids in enhancing transfection is the size of their headgroups. Formulations containing cationic lipids with "relatively small polar headgroups" have been predicted to be most useful (Felgner, et al., J. Biol. Chem. 269(4): 2550–2561 (1994)). In addition, Morris-Natschke, et al., (J. Med. Chem. 36: 2018–2025 (1993)) describe the use of phosphocholine ether lipids, including a sulfonium derivative, as anti-neoplastic agents, and report that the presence of large headgroup substituents decreased efficacy.

Because of the physiochemical properties of the sulfonium ion, a thiocationic lipid with a larger headgroup may be preferred. Particularly, when the lipid headgroup consists of a sulfur atom surrounded by adjoining saturated carbons, the sulfonium ion will exhibit a diffusion of charge to the neighboring carbons that may facilitate interaction of the lipid with cellular membranes, as well as decreasing toxicity.

Although the previously described ammonium and sulfonium ion-containing lipids have been shown to be useful in many therapeutic applications, their incorporation into and use in the form of complex liposomal formulations has yet to be optimized. In particular, the enhanced efficacy which is achieved by incorporating Vitamin D into cationic lipid-containing formulations has not been explored.

It is therefore an object of the present invention to provide thiocationic lipids which are less toxic in pharmaceutical formulations than their ammonium ion-containing counterparts.

It is also an object of the present invention to provide thiocationic lipid-containing pharmaceutical formulations which enhance the intracellular delivery of biomolecules to a greater extent than previously described lipophilic compounds.

It is a further object of the present invention to provide cationic lipid-containing liposome formulations which demonstrate superior efficacy.

SUMMARY OF THE INVENTION

The present invention relates to novel sulfonium ion-containing cationic lipids ("thiocationic lipids") and their use in pharmaceutical formulations for the intracellular delivery of biomolecules. These novel compounds are glycerolipids with headgroups which contain a sulfonium ion surrounded by at least three neighboring carbon atoms that serve to beneficially diffuse the positive charge of the sulfonium ion.

In particular, the present invention relates to thiocationic lipids of the general formula:

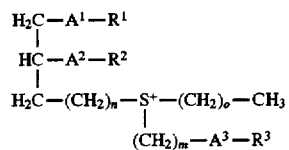

and optical isomers and/or salts thereof wherein:

$A^1$ and $A^2$ are the same or different and are —O—CO—, —O—, —S—CO— or —S—;

$A^3$ is —O—, —O—CO—, —CO—O—, —S—, —S—CO—, —CO—S—, —O—CS—, —CS—O—, —CO—NH—, —NH—CO—, —CS—NH—, —NH—CS—, —NH—CO—O—, —NH—CO—NH—, —O—CO—NH—, or is absent;

$R^1$ and $R^2$ are the same or different and are H, or $C_1$ to $C_{23}$ saturated or partially unsaturated alkyl or aralkyl, with the proviso that at least one of $R^1$ and $R^2$ is not H;

$R^3$ is a $C_1$ to $C_{12}$ alkyl, aralkyl, alkaryl, heterocyclyl or heteroaryl; or $R^3$ is an amino acid, a dipeptide, a tripeptide, a tetrapeptide or a pentapeptide; or

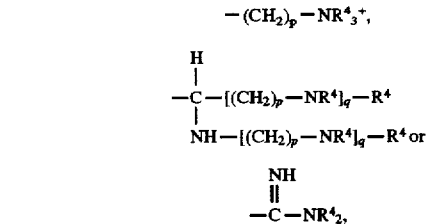

wherein p is 1 to 5, q is 0 to 4, and $R^4$ is H or a $C_1$ to $C_4$ alkyl; and m, n and o are 0 to 8 with the provisos that m $\geq$ 1 and m+n+o$\geq$3.

These cationic lipids may be used in pharmaceutical formulations in the form of complexes with a biomolecule either alone or in combination with other lipid substituents. Alternatively, they may be covalently conjugated to biomolecules and used as such in pharmaceutical formulations.

Pharmaceutical formulations according to the present invention consist of these complexes or conjugates and a pharmacologically acceptable carrier. Examples of pharmacologically acceptable carriers include aqueous solutions and complex delivery systems. Preferably, the pharmacologically acceptable carrier is a liposome.

An important aspect of the present invention is the discovery that certain cationic lipid-containing liposome formulations for use in the intracellular delivery of biomolecules exhibit enhanced efficacy. Such liposomes generally consist of an ammonium or sulfonium ion-containing lipid, Vitamin D, a pH sensitive amphiphile, and a biomolecule.

Other features and advantages of the invention are apparent from the following detailed description and the claims.

DETAILED DESCRIPTION OF THE PREFERRED EMBODIMENT

Figure 1:
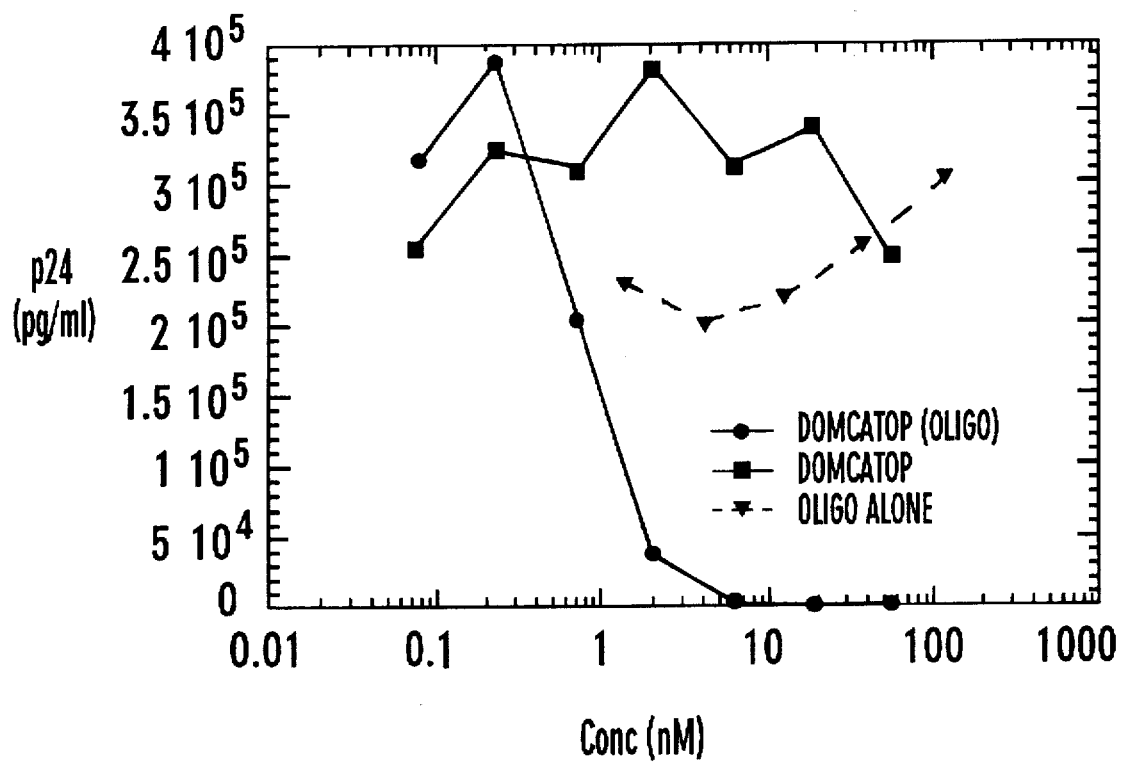
FIG. 1 illustrates the viral inhibition of a liposome formulation containing DOMCATOP and an anti-HIV antisense oligonucleotide.

The present invention provides a new class of synthetic thiocationic lipids that possess a sulfonium ion in the lipid head group. These thiocationic lipids are useful for enhancing the intracellular delivery of biomolecules by serving as constituents of covalent conjugates and/or components of pharmaceutical formulations. In order to more clearly describe the subject matter of the present invention, certain terms used herein shall be defined as follows unless otherwise indicated:

Alkaryl: "Alkaryl" means an aryl group bearing at least one alkyl substituent, for example tolyl or t-butylphenyl.

Alkenyl: "Alkenyl" means an alkyl group or moiety having at least two carbons joined to each other by a double bond.

Alkyl: "Alkyl" means straight chain or branched chain hydrocarbon group or moiety. When used alone, the term alkyl refers to a fully saturated hydrocarbon group.

Alkynyl: "Alkynyl" means an alkyl group or moiety having at least two carbons joined by a triple bond.

Amphiphilic: "Amphiphilic", when used to refer to an organic compound, means that the compound consists of both a hydrophobic (non-polar) moiety and a hydrophilic (polar) moiety. Examples of amphiphilic compounds include sodium oleate; phosphatidylcholine and derivatives thereof, such as dioleylphosphatidylcholine ("DOPC"); and dioleylphosphatidylethanolamine ("DOPE").

Antisense Oligonucleotide: "Antisense oligonucleotide" means an oligonucleotide which is complementary to a target "sense" nucleic acid, and functions at least partially by sequence-specific mechanisms to regulate the functioning of the target nucleic acid.

Aralkyl: "Aralkyl" means an alkyl group to which is attached at least one aryl ring moiety, for example benzyl, phenethyl or benzhydryl.

Aryl: "Aryl" means an aromatic hydrocarbon group or moiety, such as phenyl or naphthyl.

Biomolecule: "Biomolecule" means an organic compound which has a desirable biological activity or function, i.e. a "biological effect", in vivo. For example, biomolecules consisting of therapeutic agents may alter cellular functions, such as gene functions. Alternatively, biomolecules consisting of diagnostic agents, such as magnetic resonance imaging ("MRI") or computerized tomography ("CT") agents, have the biological function of enhancing the diagnostic images of tissues and/or organs.

Complementary: "Complementary", when used to refer to a nucleic acid, means a nucleic acid of one polarity containing a sequence of nucleotides whose bases pair via Watson-Crick hydrogen bonds with the nucleotide bases of another nucleic acid of opposite polarity, i.e. adenine ("A") pairs with thymine ("T") or uracil ("U"), and guanine ("G") pairs with cytosine ("C"). For example, a nucleic acid having the sequence GCAU in the 5' to 3' direction is "complementary" to a nucleic acid having the sequence CGTA in the 3' to 5' direction. Use of the term complementary herein is intended to include those nucleic acids which are substantially complementary. Complementary nucleic acids can also be referred to as one being the plus ("(+)") or "sense" strand and the other being the minus ("(−)") or "antisense" strand.

Complex: "Complex" means a non-covalent physical, usually ionic, association between two or more compounds. Examples of complexes include, for example, a negatively charged oligonucleotide which is ionically associated with a cationic lipid.

DODMECAP: "DODMECAP" means 1,2-dihexadecyloxy-3-(N-(5-carboxypentyl)-N,N-dimethylammonio)propane, and isomers and/or salts thereof.

DODMEHAP: "DODMEHAP" means 1,2-dihexadecyloxy-3-(N-(6-hydroxyhexyl)-N,N-dimethylammonio)propane, and isomers and/or salts thereof.

DOMCATOP: "DOMCATOP" means S-((2,3-dihexadecyloxy)propyl)-S-(5-carboxypentyl)methylsulfonium, and isomers and/or salts thereof.

DOMHYTOP: "DOMHYTOP" means S-((2,3-dihexadecyloxy)propyl)-S-(6-hydroxyhexyl)methylsulfonium, and isomers and/or salts thereof.

DOPC: "DOPC" means dioleylphosphatidylcholine.

DOPE: "DOPE" means dioleylphosphatidylethanolamine.

Glycerolipid: "Glycerolipid" means a lipophilic molecule bearing a glycerol backbone, at least one hydrophobic tail, and which may also contain a hydrophylic polar headgroup.

Headgroup: "Headgroup" means that portion of a glycerolipid which is attached to the glycerol backbone at one of the terminal carbons. Headgroups can be neutral or polar.

Heteroaryl: "Heteroaryl" means an aromatic group bearing at least one heteroatom as part of the aromatic ring structure, for example pyrrolo or pyridyl.

Heterocyclyl: A cyclic group bearing at least one heteroatom as part of the ring structure, for example piperidinyl, pyrrolidinyl or morpholino.

Hybridize: "Hybridize" means the formation of a duplex between complementary nucleic acids via base pair interactions.

Liposome: "Liposome" means a vesicle composed of amphiphilic lipids arranged in a spherical bilayer or bilayers.

Modified: "Modified", when used to refer to a nucleic acid, means a nucleic acid in which any of the natural structures have been altered. These include modifications to the phosphodiester linkages, the sugars (ribose in the case of RNA or deoxyribose in the case of DNA) and/or the purine or pyrimidine bases. Modified phosphodiester linkages include phosphorothioates, phosphotriesters, methylphosphonates and phosphorodithioates.

Nucleic Acid Sequence: "Nucleic acid sequence", or "sequence", means both a nucleic acid having a particular sequence of nucleotides, and also the sequence or order of nucleotides present in a particular nucleic acid. Which of these two meanings applies will be apparent form the context in which this term is used.

OBEHYTOP: "OBEHYTOP" means S-((2-benzyloxy-3-octadecyloxy)propyl)-S-(6-hydroxyhexyl)methylsulfonium, and isomers and/or salts thereof.

OBECATOP: "OBECATOP" means S-((2-benzyloxy-3-octadecyloxy)propyl)-S-(5-carboxypentyl)methylsulfonium.

OA: "OA" means oleic acid.

Oligonucleotide: "Oligonucleotide" means a short segment of a nucleic acid.

Pharmacologically compatible carrier: "Pharmacologically compatible carrier" means a formulation to which a biomolecule can be added to facilitate its administration to a patient without exhibiting any unacceptable levels of toxicity or pharmacologically adverse effects.

Phosphorothioate oligonucleotide: "Phosphorothioate oligonucleotide" means an oligonucleotide having all phosphorothioate linkages in place of naturally occurring phosphodiester linkages.

Polyanion: "Polyanion" means a molecule bearing more than one negative charge.

Sequence: "Sequence" means the pattern or order of the nucleotide bases (A, G, C, T or U) in a nucleic acid.

Therapeutically effective amount: "Therapeutically effective amount" means an amount which is sufficient to demonstrate a biological effect which is sufficient to produce a desired therapeutic benefit.

The usefulness of the thiocationic lipids of the present invention is enhanced by the presence of a well-distributed positive charge in the lipid headgroup, which allows for efficient interaction with negatively charged cellular membranes. The preferred use of these thiocationic lipids is in the intracellular delivery of negatively charged biomolecules. The thiocationic lipids also function to balance the negative charges on such biomolecules which makes the resultant formulations more charge neutral. A particularly preferred use is in the intracellular delivery of oligonucleotides, for example phosphorothioate oligonucleotides. They may also be useful in the intracellular delivery of certain diagnostic imaging agents, such as iodine-containing CT agents.

The thiocationic lipids of the present invention are designed to mimic naturally occurring cellular membrane constituents. This allows the thiocationic lipid, and any associated biomolecule, to fuse with the cellular membrane thus facilitating intracellular delivery. Without being able to efficiently fuse with cellular membranes (which is sometimes referred to as a substance's "fusogenic" property), foreign objects are phagocytized and quickly degraded by lysosomal enzymes.

I. Thiocationic Glycerolipid Structure

The novel thiocationic lipids of the present invention can be represented by the general formula of Structure I:

Structure I

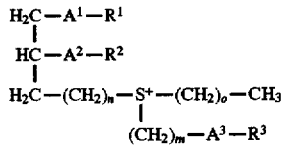

and optical isomers and/or salts thereof.

The thiocationic lipids given by Structure I can be described as having three separate moieties; a backbone, one or more tailgroups and a headgroup. As given above, the backbone is composed of the three-carbon glycerol moiety; the tailgroups are given by $R^1$ and $R^2$, and are attached to the backbone via $A^1$ and $A^2$; and the headgroup is given by;

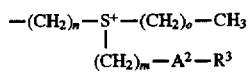

The thiocationic glycerolipids of the present invention contain a positively charged sulfonium ion, $S^+$. The sulfonium ion has the advantage of providing a lower charge density as compared to a positively charged ammonium ion. In combination with the surrounding carbons in the headgroup, the positive charge is diffused, thus permitting enhanced interactions with negatively charged cell surfaces, as well as improved efficacy. Thus, m, n and o are each from 0 to 8, with the proviso that $m \geq 1$, and $m+n+o \geq 3$.

$A^1$ and $A^2$ provide the linkage between the glycerol backbone and the lipophilic tails. $A^1$ and $A^2$ can be the same or different and are —O—CO—, —O—, —S—CO— or —S—. Particularly preferred embodiments are compositions wherein both $A^1$ and $A^2$ are —O—, and $R^1$ and $R^2$ are long chain (C16 to C18) alkyl moieties linked to $A^1$ and $A^2$ via a —$CH_2$— moiety. These long chain alkyl ether lipids are metabolically more stable than ester based lipids, and have been found to be superior in transporting nucleic acids into cells. A particularly preferred compound of this type is DOMHYTOP, or its carboxyacid derivative, DOMCATOP. See Example I Parts A and B, respectively.

Another aspect of the present invention is the ability to vary the hydrocarbon chain length of the $R^2$ moiety in order to selectively manipulate the formation of preferred liposome structures. For example, when $A^2$ is —O— and $R^2$ is H, the glycerolipid (i.e. "lysolipid") thus formed will have a single tailgroup. Use of lysolipids in combination with lipids having longer chain $R^2$ moieties may favor the formation of liposomes having one or more bilayers. Use of lysolipids alone favors the formation of micelles. Such mixed lipid formulations can be optimized for size and cellular uptake by varying the ratio of components accordingly.

Another preferred class of thiocationic lipids according to the present invention are compounds wherein $A^2$ is —O—, and $R^2$ is the aralkyl $CH_2C_6H_5$. These benzyl derivatives have increased hydrophobicity due to the presence of the aromatic moiety, and as such may exhibit preferred formulation characteristics. A particularly preferred compound of this variety is OBEHYTOP, or the equivalent carboxyacid derivative, OBECATOP. See Example I Parts C and D, respectively.

It is also possible to incorporate $R^1$ and $R^2$ moieties having varying degrees of unsaturation in order to optimize the fusogenic properties and formulation characteristics.

Other novel thiocationic lipids provided by the present invention are molecules possessing additional cationic groups which are incorporated into the molecule in the $R^3$ position. In the preferred embodiments of this family of cationic lipids, the additional cationic moieties are derived from the attachment of, for example, amino acids such as lysine, arginine, histidine or tryptophan.

The $R^3$ is linked to the thiocationic lipid via $A^3$, which may be —O—, —O—CO—, —CO—O—, —S—, —S—CO—, —CO—S—, —O—CS—, —CS—O—, —CO—NH—, —NH—CO—, —CS—NH—, —NH—CS—, —NH—CO—O—, —NH—CO—NH—, —O—CO—NH—, or may be absent. The choice and/or need for a linker would be easily determined by one of skill in the art.

The thiocationic lipids of the present invention can readily be synthesized using known methods. Typically, a lipid alcohol, such as that derived from glycerol, is converted to its bromo derivative using a brominating reagent such as a mixture of carbon tetrabromide and triphenyl phosphine. The bromo derivative thus formed is then reacted with the sodium salt of an alkyl mercaptan, such as sodium thiomethoxide, so as to obtain the alkyl thioglycerol intermediate. Alkylation of this intermediate is carried out via refluxing in the presence of a haloalkyl compound using an appropriate solvent, if necessary, to provide the cationic lipid as its halide salt.

Thiocationic Lipid-Biomolecule Conjugates

The thiocationic lipids of the present invention can also be in the form of compositions comprising the thiocationic lipid covalently conjugated to biomolecules.

The biomolecule can be any organic compound which exhibits a desirable biological effect, and which is capable of retaining this biological effect after conjugation to the cationic lipid. Examples of biomolecules include, but are not limited to, proteins, hormones, genes, polypeptides, oligonucleotides, nucleosides, drugs, antibiotics, antibodies, diagnostic imaging agents, and derivatives and analogues thereof. Covalent linkages between the thiocationic lipid and the biomolecules can be accomplished using any known methods. See, for example, PCT WO 94/05624.

The biomolecule is preferably an oligonucleotide, and more preferably a phosphorothioate oligonucleotide for purposes of resistance to degradative nucleases. In addition, the oligonucleotide may be RNA or DNA, but is more preferably DNA for purposes of resistance to RNases. Oligonucleotides which are useful in pharmaceutical formulations will typically have a nucleotide sequence that is either of interest or is sufficiently complimentary to hybridize to a nucleotide sequence of interest. The oligonucleotide typically is capable of performing a biochemical function in receptor host cells and/or altering the operation of the cellular machinery. Examples of such functions are as transfection or antisense agents.

Although appropriate oligonucleotide length depends entirely on the particular use for which the oligonucleotide is designed, certain generalizations are possible. If the oligonucleotide is to be used as an antisense therapeutic agent, it will preferably be between about 12 and 50, and more preferably between about 15 and 30 nucleotides in length.

The oligonucleotides that may be used with the present invention include, but are not limited to, naturally occurring nucleic acids, and modified nucleic acids such as those having phosphorothioate, methylphosphonate or phosphorodithioate internucleotide linkages. In addition, the biomolecule can be a naturally occurring nucleoside, such as adenosine, guanosine, cytidine, thymidine and uridine or analogues thereof such as 5-fluorouridine, 5-alkyluridine, deazaguanosine, azaguanosine, azathymidine.

The site of attachment of a phosphorothioate oligonucleotide to the thiocationic lipids of the present invention may be via either the 5' or 3' terminus, the internucleotide linkages, the nucleoside bases or the backbone sugar moieties. Such linkages can be accomplished using any known methods. For example, see Goodchild, et al., Bioconjugate Chemistry 1(3): 165-187 (1990). The cationic lipid may be attached via $A^3$ and/or $R^3$ to the 3'-OH or 5'-OH. Alternatively, the cationic lipid may be attached via $A^3$ and/or $R^3$ at any internucleotide linkage, such as via the O or S atoms in the internucleotide phosphorothioate linkage. In addition, the cationic lipid may be attached to a base via $A^3$ and/or $R^3$ to an endocyclic ring C or N, or to an exocyclic N or O. It may also be attached via $A^3$ and/or $R^3$ to the 1', 2' or 4' position of a sugar moiety.

II. Cationic Lipid Formulations

The pharmaceutical formulations employing the thiocationic lipids described herein may be composed of thiocationic lipid-biomolecule conjugates, or they may be composed of cationic lipid-biomolecule complexes which are formed by mixing together the thiocationic lipids and the biomolecules described herein under conditions in which a stable association via ionic and/or hydrophobic interactions between the lipid and the biomolecule is formed. In both cases, the thiocationic lipid-biomolecule conjugates/complexes are prepared and administered in a pharmacologically acceptable carrier. Examples of pharmacologically acceptable carriers include aqueous solutions such as water, saline, buffers or carbohydrate solutions; and complex delivery systems such as liposomes, microspheres, or emulsions.

III. Liposome Formulations

The thiocationic lipid-containing biomolecule formulations of the present invention preferably consist of liposomes. Any of the aforementioned biomolecules can be encapsulated into liposomes. In addition, numerous biomolecule-containing liposome formulations are described in the literature, and serve as examples of additional biomolecules suitable for encapsulation using the liposome formulations described herein.

Lipid aggregates can take the form of completely closed structures made up of a lipid bilayer containing an encapsulated aqueous volume (i.e. unilamellar liposomes), or they may contain more than one concentric lipid bilayer separated by an aqueous volume (i.e. multilamellar liposomes). Each lipid bilayer is composed of two lipid monolayers, each of which has a hydrophobic (nonpolar) "tail" region and a hydrophilic (polar) "head" region. In the bilayer, the hydrophobic "tails" of the lipid monolayers orient toward the inside of the bilayer, while the hydrophilic "heads" orient toward the outside of the bilayer. It is within the aqueous phase that the biomolecule becomes entrapped in the liposome, unless the biomolecule is in the form of a lipid-biomolecule conjugate, in which case the biomolecule may become embedded within the bilayer.

Liposomes may be made by a variety of techniques known in the art. (See, for example, Bangham et al., J. Mol. Biol., 13: 238–252(1965)). These methods generally involve first dissolving and mixing the lipids in an organic solvent, followed by evaporation. Then an appropriate amount of the aqueous phase is mixed with the lipid phase, and then allowed to incubate for a sufficient time for the liposomes to form. The aqueous phase will generally consist of the biomolecule in suspension with other solutes, such as buffers or sugars.

In addition to the biomolecule to be encapsulated, the liposomes of the present invention are comprised of the thiocationic lipids described herein alone, a mixture of thiocationic lipids described herein or the thiocationic lipids of the present invention combined with other known lipids, such as an anionic lipid (for example, phosphatidylglycerol, phosphaticid acid or a similar anionic phospholipid analog), or a neutral lipid (for example, phosphatidylcholine or phosphatidylethanolamine). The present liposomal formulations may further include a lysolipid, such as lysophosphatidylcholine, lysophosphatidylethanolamine, or a lyso form of a cationic lipid species.

The liposome can also include optional substituents, such as sterols, glycolipids, tissue or organ targeting substances such as antibodies or proteins, fatty acids, or any other natural or synthetic lipophilic or amphiphilic compounds.

Suitable sterols for inclusion into the liposomes include, but are not limited to, cholesterol and Vitamin D, and are included in the liposome formulations as stabilizers.

The molar ratio of thiocationic lipid to total lipid must be sufficient to result in the formation of a liposome with an overall positive charge. This amount will depend on the charge and amount of the encapsulated biomolecule, as well as the charge and amount of other constituents of the liposome. Generally, the liposome will contain from about 9:1 to 1:9 molar ratio of cationic lipid to total lipid, and preferably about 1:2 to 2:1. The molar ratio of total lipid to biomolecule is from about 200:1–100:1, and is preferably about 160:1.

IV. Liposome Formulations with Enhanced Efficacy

An important aspect of the present invention is the discovery that the efficacy of cationic lipid-biomolecule liposome formulations is enhanced by the presence of Vitamin D, and at least one pH sensitive amphiphilic lipid. Both ammonium ion and sulfonium ion-containing cationic lipids are useful in such liposome formulations for the intracellular delivery of biomolecules.

The cationic lipid may be any of the thiocationic lipids described herein, or any other known ammonium or sulfonium ion-containing cationic lipids. As described above, the cationic lipid may be used alone or in combination with other cationic, neutral or anionic lipids.

The Vitamin D may be Vitamin $D_3$ (also called "cholecalciferol"), or any analogue or derivative of Vitamin D which does not significantly diminish the overall efficacy-enhancing effects of Vitamin D, herein collectively referred to as "Vitamin D". Preferably, underivatized Vitamin $D_3$ is employed.

Some amphiphiles have the ability to change their charge as a function of pH and are therefore "pH sensitive". For example, liposomal vesicles containing pH sensitive amphiphiles such as oleic acid and/or DOPE can change their charge as a function of pH, while DOPC containing vesicles do not change their charge in a pH dependent fashion. The ability of an amphiphile to change its charge as a function of pH depends on the other constituents of the liposome. In particular, the degree of alkyl chain saturation may have an effect. In addition, there may be ion-pairing interactions between the negative charges of the amphiphile, such as the negatively charged phosphate in DOPE, and the positively charged headgroups in the cationic lipids. This would leave the positively charged amino group in the DOPE susceptible to a change in charge as a function of pH. (See Felgner et al., J. Bio. Chem. 269:1–12 (1994)).

The pH sensitivity of the amphiphile serves to enhance the fusogenicity of the liposomal vesicles with endosomal membranes within the cell (Ropert et al., Biochem. Biophys. Res. Commun. 183(2): 879–85 (1992)). Suitable pH sensitive amphiphilic lipids include, but are not limited to DOPE and oleic acid. Preferably, the pH sensitive amphiphile is oleic acid, but any lipophilic amphiphiles which are susceptible to a change in charge as a function of pH at or near physiological pH (around 6 to 7.5) after incorporation into the liposome are suitable for use.

A particularly preferred liposome formulation for the intracellular delivery of oligonucleotides consists of cationic lipid:oleic acid:Vitamin $D_3$ in the molar ratio of 10:5:2. Other molar ratios can be designed to maximize the efficacy of liposomal formulations consisting of different constituents and/or biomolecules. Such molar ratios can easily be determined using known techniques. See, for example, Liposome Technologies, CRC Press, publishers, Gregory Gregoriadis, ed. (1984).

V. Delivery of Pharmaceutical Formulations

The thiocationic lipids of the invention can be used in pharmaceutical formulations to deliver biomolecules by various routes and to various sites in the animal body to achieve a desired therapeutic effect. These pharmaceutical formulations may consist of thiocationic lipid-biomolecule complexes and/or thiocationic lipid-biomolecule conjugates in any of the aforementioned pharmacologically acceptable carriers.

Local or systemic delivery of the formulation can be achieved by administration comprising application or insertion of the formulation into body cavities, inhalation or insufflation of an aerosol, or by parenteral introduction, comprising intramuscular, intravenous, intradermal, peritoneal, subcutaneous and topical administration.

Orally administered formulations may be in the form of solids, liquids, emulsions, suspensions, or gels, or preferably in dosage unit form, for example as tablets or capsules. Tablets may be compounded in combination with other ingredients customarily used, such as talc, vegetable oils, polyols, gums, gelatin, starch, and other carriers.

Parenteral formulations intended for injection, either subcutaneously, intramuscularly, or intravenously, can be prepared either as liquids or solid forms for suspension in liquid prior to injection, or as emulsions. Such preparations are sterile, and liquids to be injected intravenously should be isotonic. Suitable excipients are, for example, water, dextrose, saline, and glycerol.

The formulations may also be administered in aerosol form to cavities of the body such as the nose, throat, or bronchial passages.

The ratio of biomolecule to the cationic lipid and the other compounding agents in these formulations will vary as the dosage form and amount requires.

Effective dosages of the formulations described herein depend on the biomolecule and its desired biological activity, as well as the particular formulation kinetics, composition, physical properties, desired therapeutic effect, subject weight, etc. Dosage optimization can easily be performed using known method.

VI. Therapeutic Uses

The preferred therapeutic use of the biomolecule formulations described above is in the intracellular delivery of a therapeutic agent comprising a liposome-encapsulated antisense oligonucleotide. A particularly preferred therapeutic agent formulation which is useful in inhibiting HIV consists of a thiocationic lipid-containing liposomes as delivery vehicles of the phosphorothioate oligonucleotide given by SEQ. ID. NO. 1. This oligonucleotide is complementary to the MRNA sequence given by SEQ. ID. NO. 2 encoding the HIV REV protein. (See Peterson, et al., Published PCT Application No. WO 95/03407.)

Experimental Procedures

The present invention can be better understood by way of the following examples that are representative of the preferred embodiments, but which are not to be construed as limiting the scope of the invention. All chemicals used herein were purchased from Aldrich Chemical Co., Milwaukee, Wis., unless otherwise noted.

EXAMPLE I

Synthesis of Cationic Lipids

Part A: Synthesis of the Bromide Salt Form of DOMHYTOP
Step 1. Synthesis of 1,2-O-Dihexadecyl-3-bromo-1,2-propanediol In a 250 ml round bottom flask equipped with a magnetic stir bar, 1.92 g (3.6 mmoles) of dihexadecylglycerol (Sigma Chemicals) was dissolved into 120 ml of toluene. To this solution were added 3.54 g (10.7 mmoles) of carbon tetrabromide and 2.80 g (10.7 mmoles) of triphenylphosphine and the reaction mixture was stirred overnight (18 hr) at room temperature. The yellow suspension was filtered and the filtrate concentrated on a rotary evaporator to afford a white solid. This residue was dissolved into toluene, washed once with saturated sodium chloride, dried over anhydrous magnesium sulfate and concentrated under vacuum on a rotary evaporator to afford 2.5 g of the crude product as a white powder. This crude product was purified by flash column chromatography on a silica gel 60 (E. Merck, Germany) column by sequential elution with 100 ml each of hexane, 1% ethyl acetate in hexane, 2% ethyl acetate in hexane and finally with 3% ethyl acetate in hexane. Fractions (8 ml) were collected and screened by thin-layer chromatography ("TLC") and those fractions that contained pure product (silica gel, 5% ethyl acetate in hexane, Rf=0.59) were pooled. The pooled fractions were concentrated under vacuum on a rotary evaporator to afford a quantitative yield of the 1,2-O-dihexadecyl-3-bromo-1,2-propanediol as a white powder.

Step 2. Synthesis of 1,2-O-Dihexadecyl-3-methylthio-1,2-propanediol

Racemic 1,2-O-dihexadecyl-3-bromo-1,2-propanediol (from Step 1), 2.0 g (3.3 mmoles), was dissolved into 100 ml of dry tetrahydrofuran in a 250 ml round bottom flask equipped with a magnetic stir bar. To this solution was added 2.33 g (33.2 mmoles) of sodium thiomethoxide powder and the reaction mixture was stirred overnight at room temperature. The reaction was monitored by TLC (silica gel, 5% ethyl acetate in hexane) and an additional 490 mg (7 mmoles) of sodium thiomethoxide was added to the reaction. After an additional 3 hr, the mixture was filtered and the filtrate was washed with 50 ml tetrahydrofuran. The combined filtrates were concentrated under vacuum using a rotary evaporator to afford a yellow residue. This residue was dissolved into 50 ml chloroform and the organic solution was washed twice with 25 ml of a concentrated solution of sodium bicarbonate. The organic phase was then dried over anhydrous magnesium sulfate and concentrated on a rotary evaporator under vacuum to afford the crude product as a pale yellow oily residue. The crude product was purified by column chromatography on a silica gel 60 (E. Merck, Germany) column using a step gradient of 0 to 10% ethyl acetate in hexane. The fractions collected were screened by TLC. Those fractions containing pure product were pooled and concentrated to afford 1,2-O-dihexadecyl-3-methylthio-1,2-propanediol in 90% yield.

Step 3. Synthesis of 1,2-O-Dihexadecyl-3-(S-methyl)-(6-hydroxyhexyl)-sulfonium bromide Racemic 1,2-O-dihexadecyl-3-methylthio-1,2-propanediol (from Step 2), 1.0 g (1.75 mmoles), was dissolved into 120 ml toluene in a 250 round bottom flask equipped with a magnetic stir bar and a reflux condenser. To this solution was added 3.17 g (17.5 mmoles) of 6-bromohexanol and the solution heated at 135° C. for 3 days. The brownish solution was then allowed to cool to room temperature and concentrated on a rotary evaporator to afford a brownish oily residue. This residue was dissolved into 50 ml chloroform and washed twice with 30 ml of a saturated sodium chloride solution. The chloroform layer was then dried over magnesium sulfate. Upon removal of the magnesium sulfate by filtration, the solution was passed through a bed of silica to remove the extremely polar impurities in the solution. This solution was next concentrated under vacuum to afford the crude product as a waxy residue. The crude product was purified by column chromatography using a silica gel 60 (E. Merck, Germany) column and eluted sequentially first with 100 ml hexane, followed by 100 ml of 10% ethyl acetate in hexane and finally with 30% ethyl acetate in hexane. Fractions containing the product as determined by TLC were pooled and concentrated to afford the bromide salt of DOMHYTOP as a low melting yellowish solid in 88% yield.

Part B: Synthesis of the Bromide Salt of DOMCATOP

Racemic 1,2-O-dihexadecyl-3-methylthio-1,2-propanediol (prepared as in Part A, Steps 1 and 2), 1.0 g (1.75 mmoles), was dissolved into 120 ml toluene in a 250 round bottom flask equipped with a magnetic stir bar and a reflux condenser. To this solution was added 3.41 g (17.5 mmoles) of 6-bromohexanoic acid and the solution heated at 135° C. for 4 days. The brownish solution was then allowed to cool to room temperature and concentrated on a rotary evaporator to afford a brownish oily residue. This residue was dissolved into 50 ml chloroform and passed through a bed of silica to remove the extremely polar impurities in the solution. The resulting solution was next washed with 30 ml of a saturated sodium chloride solution. The chloroform layer was then dried over anhydrous magnesium sulfate. Upon removal of the magnesium sulfate by filtration, the solution was concentrated under vacuum to afford the crude product as a yellowish oily residue. This crude product was purified by column chromatography using a silica gel 60 (E. Merck, Germany) column, eluting sequentially with 100 ml of hexane, followed by 10 ml of 10% ethyl acetate in hexane and finally with 30% ethyl acetate in hexane. Fractions from the 30% ethyl acetate in hexane eluates contained the product as determined by TLC and were pooled and concentrated to afford the bromide salt of DOMCATOP as a low melting yellowish solid in 42% yield.

Part C: Synthesis of the Bromide Salt of OBEHYTOP

Step 1. Synthesis of 1-O-Octadecyl-2-O-benzyl-3-bromo-1,2-propanediol

In a 250 ml round bottom flask equipped with a magnetic stir bar, 2.00 g (4.6 mmoles) of 1-O-octadecyl-2-O-benzylglycerol (Bachem, Switzerland) was dissolved into 120 ml of toluene. To this solution were added 4.58 g. (13.8 mmoles) of carbon tetrabromide and 3.62 g. (13.8 mmoles) of triphenylphosphine and the reaction mixture stirred for 4 hours at room temperature. The yellow suspension was filtered and the filtrate concentrated on a rotary evaporator to afford a white solid. This residue was dissolved into 50 ml chloroform, washed twice with 30 ml saturated sodium bicarbonate, dried over anhydrous magnesium sulfate and concentrated under vacuum on a rotary evaporator to afford 2.5 g of the crude product as a white powder. This crude product was purified by flash column chromatography on a silica gel 60 (E. Merck, Germany) column by sequential elution with 100 ml each of hexane, 1% ethyl acetate in hexane, 2% ethyl acetate in hexane and finally with 3% ethyl acetate in hexane. Fractions collected were screened by TLC and those fractions that contained pure product (silica gel, 5% ethyl acetate in hexane, Rf=0.56) were pooled. The pooled fractions were concentrated under vacuum on a rotary evaporator to afford a quantitative yield of the 1-O-octadecyl-2-O-benzyl-3-bromo-1,2-propanediol as a white powder.

Step 2. Synthesis of 1-O-Octadecyl-2-O-benzyl-3-methylthio-1,2-propanediol

Racemic 1-O-octadecyl-2-O-benzyl-3-bromo-1,2-propanediol, 1.99 g (4.0 mmoles), was dissolved into 100 ml of dry tetrahydrofuran in a 250 ml round bottom flask equipped with a magnetic stir bar. To this solution was added 2.8 g (40.0 mmoles) of sodium thiomethoxide powder and the reaction mixture stirred for 4.5 hours at room temperature. The reaction was monitored by TLC (silica gel, 5% ethyl acetate in hexane; Rf=0.51). The mixture was filtered and the filtrate was washed with 50 ml tetrahydrofuran. The combined filtrates were concentrated under vacuum using a rotary evaporator to afford a yellow residue. This residue was dissolved into 50 ml chloroform and the organic solution washed twice with 30 ml of a concentrated solution of sodium bicarbonate. The organic phase was then dried over anhydrous magnesium sulfate and concentrated on a rotary evaporator under vacuum to afford the crude product as a pale yellow oily residue. This crude product was purified by chromatography on silica gel 60 (E. Merck, Germany) using a step gradient of 0 to 10% ethyl acetate in hexane. The fractions collected were screened by TLC. Those fractions containing pure product (silica gel, 5% ethyl acetate in hexane, Rf=0.51) were pooled and concentrated to afford 1-O-octadecyl-2-O-benzyl-3-methylthio-1,2-propanediol in 90% yield.

Step 3. Synthesis of 1-O-Octadecyl-2-O-benzyl-3-(S-methyl-S-(6-hydroxyhexyl))-sulfonium bromide Racemic 1-O-octadecyl-2-O-benzyl-3-methylthio-1,2-propanediol, 1.02 g (2.2 mmoles), was dissolved into 120 ml toluene in a 250 ml round bottom flask equipped with a magnetic stir bar and a reflux condenser. To this solution was added 3.98 g. (22.0 mmoles) of 6-bromohexanol and the solution heated at 135° C. for 3 days. The brownish solution was then allowed to cool to room temperature and concentrated on a rotary evaporator to afford a brownish oily residue. This residue was dissolved into 50 ml chloroform and passed through a bed of silica to remove the extremely polar impurities in the solution. The resulting solution was next washed twice with 30 ml of a saturated sodium bicarbonate solution, followed by extraction with 30 ml of a saturated sodium chloride solution. The chloroform layer was then dried over anhydrous magnesium sulfate. Upon removal of the magnesium sulfate by filtration, the solution was concentrated under vacuum to afford the crude product as a yellowish oily residue. This crude product was purified by column chromatography using silica gel 60 (E. Merck, Germany), eluting sequentially with 100 ml of hexane, followed by 100 ml of 10% ethyl acetate in hexane and finally with 30% ethyl acetate in hexane. Fractions containing the product as determined by TLC (silica gel, 30% ethyl acetate in hexane, Rf=0.41) were pooled and concentrated to afford the bromide salt of OBEHYTOP as a low melting yellowish solid in 85% yield.

Part D: Example 4: Synthesis of the Bromide Salt of OBECATOP

Racemic 1-O-octadecyl-2-O-benzyl-3-methylthio-1,2-propanediol (prepared as in Part C, Steps 1 and 2), 1.0 g (1.75 mmoles), was dissolved into 120 ml toluene in a 250 round bottom flask equipped with a magnetic stir bar and a reflux condenser. To this solution was added 4.30 g (22.0 mmoles) of 6-bromohexanoic acid and the solution heated at 135° C. for 3 days. The brownish solution was then allowed to cool down to room temperature and concentrated on a rotary evaporator to afford a brownish oily residue. This residue was dissolved into 50 ml chloroform and passed through a bed of silica to remove the extremely polar impurities in the solution. The resulting solution was next washed with 30 ml of a saturated sodium chloride solution. The chloroform layer was then dried over anhydrous magnesium sulfate. Upon removal of the magnesium sulfate by filtration, the solution was concentrated under vacuum to afford the crude product as a yellowish oily residue. This crude product was purified by column chromatography using silica gel 60 (E. Merck, Germany), eluting sequentially with 100 ml of hexane, followed by 100 ml of 10% ethyl acetate in hexane and finally with 30% ethyl acetate in hexane. Fractions containing the product as determined by TLC (silica gel, 30% ethyl acetate in hexane, Rf=0.36) were pooled and concentrated to afford the bromide salt of OBECATOP as a low melting yellowish solid in 40% yield.

Part E: Synthesis of the Bromide Salt of DODMECAP

Step 1. Bromination of 1,2-dihexadecyloxy glycerol:

1 g of 1,2-dihexadecyloxy glycerol was dissolved in 80 ml toluene in a 100 ml round bottom flask. To this solution, 1.84 g carbon tetrabromide and 1.46 g triphenylphosphine were added. The reaction mixture was stirred at room temperature for 24 hr, and the progress of the reaction monitored by thin-layer-chromatography (5% ethyl acetate in hexane).

The resulting yellowish solid was filtered and the filtrate concentrated on a rotary evaporator and dissolved in acetone. This step was repeated to isolate the product in the form of a white solid (yield 900 mg).

Step 2. Formation of 1,2-dihexadecyloxy-3-dimethylamino glycerol.

900 mg of 3-bromo-1,2-dihexadecyloxy glycerol was dissolved in 30 ml chloroform in a 100 ml round bottom flask. 720 mg dimethylamine was added to yield an approximately 10 fold molar excess, and the reaction mixture stirred at room-temperature overnight. The progress of the reaction was measured by thin-layer-chromatography (30% ethyl acetate in hexane).

The reaction mixture was transferred to a separating funnel and washed twice with saturated aqueous sodium chloride. The organic layer was dried on magnesium sulfate and then filtered. The filtrate was concentrated on a rotary evaporator to yield 630 mg product.

Step 3. Formation of the Bromide Salt of DODMECAP 270 mg of 1,2-dihexadecyloxy-3-dimethylamino glycerol from Step 2, 0.628 g bromohexanoic acid and 0.271 g potassium carbonate were dissolved in 80 ml toluene in a 100 ml round bottom flask. The reaction mixture was heated to 120° C. in an oil bath and the conditions maintained overnight along with continuous stirring. The progress of the reaction was monitored using thin-layer-chromatography (30% ethyl acetate in hexane) and was shown to be complete in 20 hr.

The reaction mixture was then concentrated on a rotary evaporator. The white residue was dissolved in 30 ml chloroform and washed thrice in a separating funnel with 30 ml deionized water. The organic layer was dried using magnesium sulfate and filtered. The filtrate was concentrated on a rotary evaporator and a white, waxy product obtained after precipitation with acetone. (yield 400 mg).

Part F: Synthesis of a Bromide Salt of DODMEHAP 630 mg of 1,2-dihexadecyloxy-3-dimethylamino glycerol from Part E, Step 2, and 1.83 g bromohexanol were dissolved in 60 ml toluene in a 100 ml round bottom flask. The reaction mixture was heated to 110° C. in an oil bath along with continuous stirring and the conditions maintained for 3 days. The progress of the reaction was monitored using thin-layer-chromatography (30% ethyl acetate in hexane) and was shown to be complete after 3 days.

The reaction mixture was concentrated on a rotary evaporator. The residue was dissolved in 30 ml chloroform and extracted with 3 washes of saturated aqueous sodium bicarbonate in a separating funnel. The organic layer was dried on magnesium sulfate and filtered. The filtrate was further concentrated on a rotary evaporator and purified on a Silica Gel 60 packed column (EM Sciences, Gibbstown, N.J.). The product was eluted using a 30% solution of ethyl acetate in hexane. Starting with 100% hexane, the concentration of ethyl acetate was gradually increased in each successive wash to 30%. (yield of product: 1.25 g).

EXAMPLE II

Synthesis of a COMCATOP-Oligonucleotide ("Liponucleotide") Conjugate

Part A: Synthesis of the NHS Ester of the Bromide Salt of DOMCATOP

The bromide salt of DOMCATOP prepared in Example I Part B (130 mg, 0.17 mmole), was dissolved in 20 ml dry tetrahydrofuran, and 65 mg (0.56 mmole) of N-hydroxysuccinimide and 116 mg (0.56 mmole) of dicyclohexylcarbodiimide were added to the solution. The solution was stirred under nitrogen for 20 hours at room temperature. The dicyclohexyl urea formed upon reaction was filtered off and the filtrate concentrated under reduced pressure to afford a residue that was dissolved into chloroform. This solution was extracted with saturated sodium bicarbonate, dried over magnesium sulfate and concentrated to afford a quantitative yield of the NHS ester of DODME-CAP.

Part B: Synthesis of a 5'-Amino Terminated Oligonucleotide

Synthesis of a 5'-amino terminated oligonucleotide consisting of SEQ. ID. NO. 1 was carried out using known standard phosphoramidite chemistry procedures and a commercially available automated synthesizer. Cyanoethyl phosphoramidites of bases adenosine, guanosine, cytosine and tyrosine and an amino-linker phosphoramidite allowed for the synthesis of the oligonucleotide via automated synthesis on a controlled pore glass solid support. The last step in the synthesis of the 5'-amino terminated oligonucleotides was the use of an aminolinker phosphoramidite (Applied Biosystems, Inc., Foster City, Calif.) so as to afford upon coupling the 5'-amino terminated oligonucleotide. Deprotection of nucleoside bases, the O-cyanoethyl group and cleavage of the support bound oligonucleotide were performed in one step by treatment with ammonium hydroxide at 55° C. for at least 15 hr. Concentration of the resulting ammonical solution afforded the 5'-amino terminated oligonucleotide, which was dissolved in water and stored for subsequent use.

Part C: Coupling of the NHS Ester of DOMCATOP to the 5'-Amino Terminated Oligonucleotide to form a Liponucleotide The phosphorothioate oligonucleotide prepared in Part B (2.2 mg in 300 µl of water) was precipitated by addition of 33 µl of 3M sodium acetate and 1 mL ethanol at −20° C. for at least 1 hour. The precipitated oligonucleotide was separated by centrifugation at 4° C. for at least 30 minutes. The supernatant was removed, the oligonucleotide-containing pellet dried on a speed vacuum for 5 minutes and dissolved into 490 µl of 0.25M HEPES solution (pH 8.1). To this solution 210 µl of pyridine and 280 µl of a 25 mM solution of the thiocationic NHS ester in pyridine were added. The resulting mixture was vortexed and allowed to react at 55° C. for at least 18 hours. The solution was transferred into a 10 ml tube, treated with 280 µl of 3M sodium acetate, 700 µl of water and 7.9 ml of ethanol at −20° C. for at least 2 hours. The resulting suspension was centrifuged at 17,000 rpm at 4° C. for 1 hour and the supernatant removed. The oligonucleotide-containing pellet obtained was dried and dissolved into 1 ml. water. This crude product was purified by reversed phase HPLC using a C8 radial pak column with a gradient of increasing methanol concentration in 0.1M ammonium acetate (pH 7).

Fractions containing the liponucleotide were pooled, concentrated and the residue was dissolved into 1–2 ml. water, treated with 0.25 ml 3M sodium acetate and 8 ml ethanol at −20° C. overnight, to afford upon centrifugation a pellet of the liponucleotide.

EXAMPLE III

Synthesis of Liposome Formulations

The liposome preparations described below contained indicated amounts of DOPE (Avanti Polar Lipids, Inc., Alabaster, Ala.); cholesterol (Avanti Polar Lipids, Inc., Alabaster, Ala.); Vitamin $D_3$ (Aldrich Chemical Co., Milwaukee, Wis.); oleic acid ("OA"; NuChek Prep Inc., Elysian, Minn.); and DODMECAP, DOMCATOP, DOMHYTOP, DODMECAP, OBEHYTOP and OBECATOP prepared as described above. All ratios given are molar ratios. Unless otherwise indicated, the molar ratio of cationic lipid:titratable amphiphile:sterol used in the preparation of liposomes herein was 10:5:2. The term "total lipids" refers to the sum of all of the components of the liposome given above. The phosphorothioate oligonucleotide referred to below is given by SEQ. ID. NO. 1.

A total of 80 µmoles of the total lipids in their desired ratios was dissolved in chloroform, and then dried and rehydrated with an aqueous solution containing 1 ml of a 0.5 mM solution of the phosphorothioate oligonucleotide in phosphate buffered saline, pH 7.4. The preparations were then vortexed and allowed to come to equilibration by overnight shaking at 37° C. to allow the vesicles to form, and then freeze-thawed. Following this, the multilamellar liposomal vesicles thus formed were extruded through polycarbonate filters of an appropriate pore size to obtain liposomes with a single bilayer. To remove any unencapsulated material, the liposomes were gel-filtered through a sizing gel column. The total amount of encapsulated oligonucleotide was determined using a hybridization protection assay. (See Arnold, et al., PCT WO 89/02476.)

EXAMPLE IV

Cellular Uptake of Liposome Formulations

A total of $2 \times 10^6$ cells (U937 cells; ATCC, Rockville, Md.) in 2 ml RPMI-1640 medium (BioWhittaker, Walkersville, Md.) with 10% fetal bovine serum (GibcoBRL, Grand Island, N.Y.) were plated in a 6-well tissue culture plate and incubated at 35° C. in 5% $CO_2$. A 100 nM solution of liposome-encapsulated or free oligonucleotide in phosphate buffered saline (pH 7.4) was introduced to the cells. After 48 hr, the cells were lysed, and the amount of oligonucleotide was determined as described in Example III.

The results indicated that liposomes which were prepared as described in Example III which contained the cationic lipids DODMECAP, DODMEHAP, DOMCATOP, DOMHYTOP, OBEHYTOP or OBECATOP in combination with oleic acid and Vitamin $D_3$ demonstrated similar oligonucleotide uptake results.

EXAMPLE V

Viral Inhibition Assay

A total of $2.8 \times 10^6$ cells (Jurkat cells; ATCC) in RPMI-1640 with 10% fetal calf serum were added to two 15 ml tubes in a total of 10 ml. The cells were centrifuged, the supernatant decanted, and cells were resuspended in 1 ml of the above medium. A 4.0 ml sample of retrovirus (HIV-$1_{IIIB}$) was added to one tube, and 4.0 ml of medium alone was added to the control. The cells were incubated for 2 hr at 37°

C. in an atmosphere of 5% $CO_2$. Free virus was washed from the cells and the cells were resuspended in 35 ml of medium.

The infected and control cells were placed in 125 μl aliquots into a 96 well tissue culture plate. Varying concentrations of liposomes prepared according to Example III, or free oligonucleotides, were added to the wells and the plates were incubated for 6 days at 37° C. in an atmosphere of 5% $CO_2$. The p24 protein levels were determined by an antigen capture assay (Coulter Immunology, Hialeah, Fla.; U.S. Pat. No. 4,886,742) using manufacturer's specifications and controls. The results are depicted in FIGS. 1, 2 and 3, with "—●—" representing the liposome with the oligonucleotide, "—■—" representing the control liposome with no oligonucleotide and "—▼—" representing the free oligonucleotide.

In FIG. 1, results are presented for liposomes prepared using the thiocationic lipid DOMCATOP with or without the oligonucleotide, and for the oligonucleotide alone. As shown, the liposome containing the oligonucleotide effectively inhibited viral replication as demonstrated by a significant reduction in p24 levels.

Figure 2:
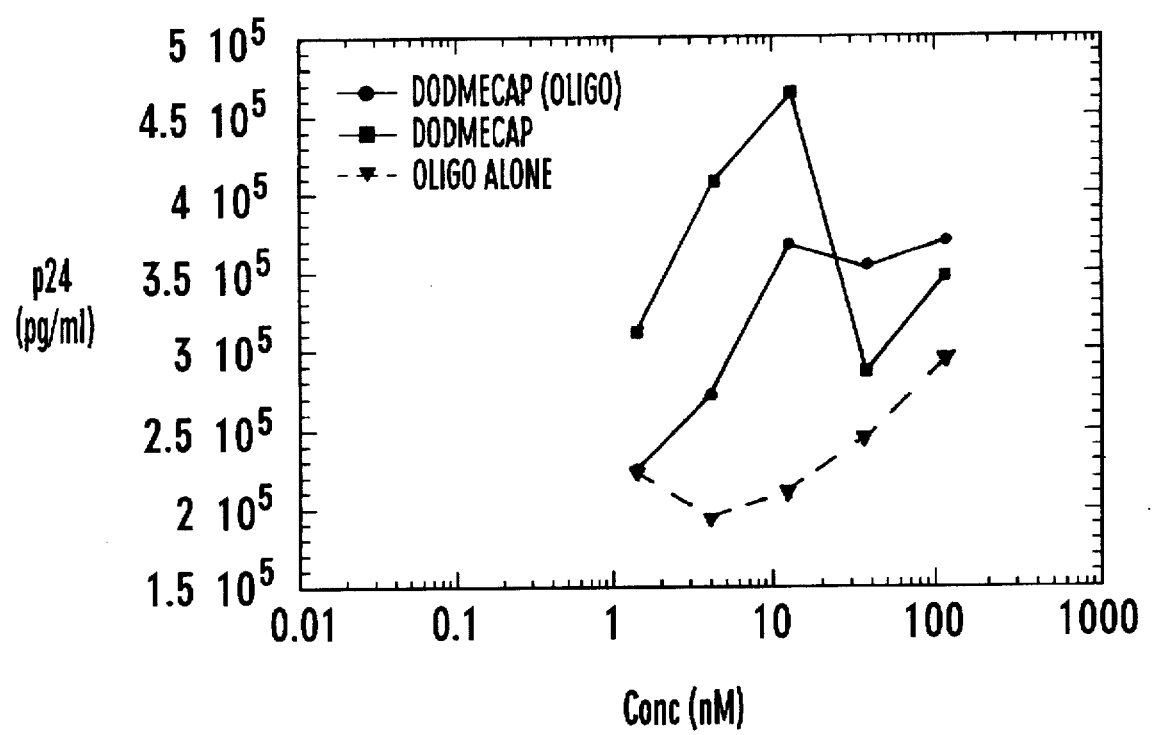
FIG. 2 illustrates the viral inhibition of a liposome formulation containing DODMECAP and an anti-HIV antisense oligonucleotide.

In FIG. 2, the results are presented with the ammonium ion-containing lipid DODMECAP. As shown, no inhibition in viral replication was observed.

Figure 3:
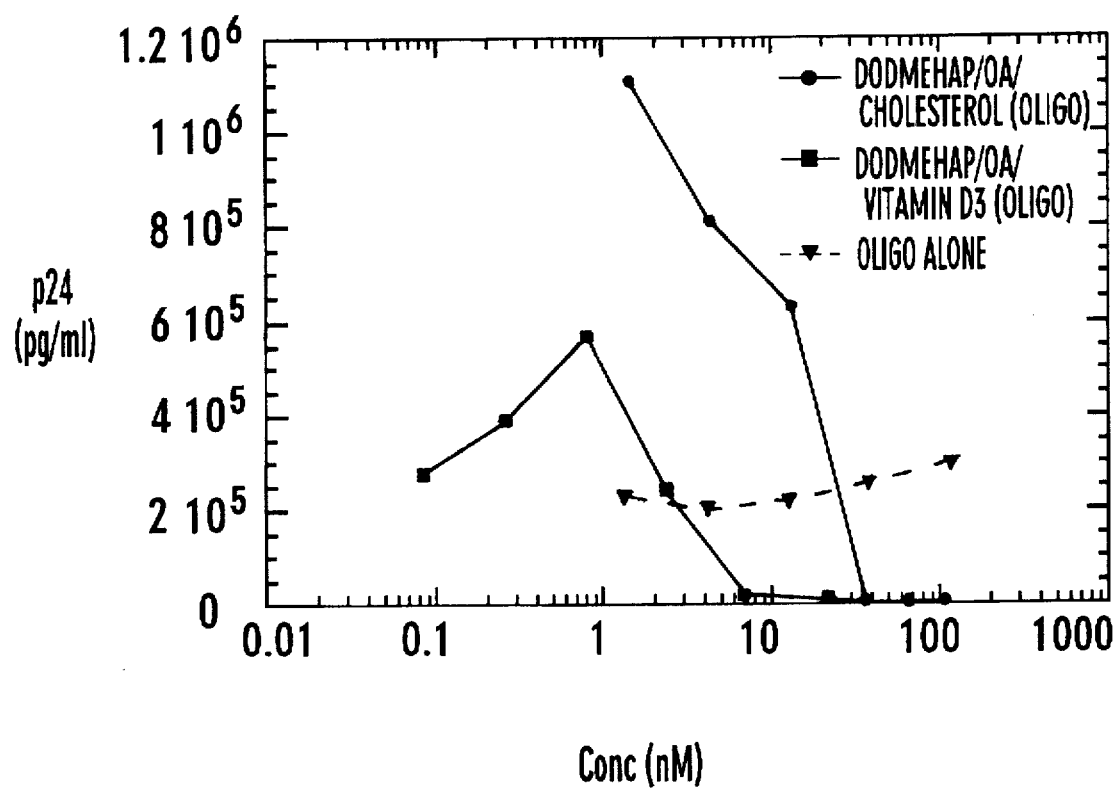
FIG. 3 illustrates the viral inhibition of a liposome formulation containing either cholesterol or Vitamin D3, and an anti-HIV antisense oligonucleotide.

In FIG. 3, the results are presented for liposomes prepared using the ammonium ion-containing lipid DODMEHAP with either Vitamin $D_3$ or cholesterol as the sterol. As shown, the Vitamin $D_3$-containing liposomes were unexpectedly more effective at inhibiting viral replication than their cholesterol-containing equivalents.

EXAMPLE VI

Cellular Metabolic Activity Assay

To determine the effects on cellular metabolic activity as a measure of the toxicity of the different liposome formulations, an XTT assay was performed on the infected cells from Example V as follows: A 1 mg/ml XTT (2,3-bis [2-methoxy-4-nitro-S-sulfophenyl]-2H-tetrazolium-S-carboxanilide inner salt; Sigma Chemical Co., St. Louis, Mo.) solution in cell medium was prepared. To this, 5 μl of 5 mM phenazine methosulfate (Sigma Chemical Co.) per ml of XTT solution was added. A 50 μl aliquot of the resultant mixture was added to each well, and the plates were incubated for 4 hr at 37° C. in an atmosphere of 5% $CO_2$. Then, 15 μl of Triton X-100 (Sigma Chemical Co.) was added to each well, and the optical density (O.D.) at 450–650 nm dual absorbancy was read. Corrected O.D. measurements were determined by subtracting the appropriate control levels.

Figure 4:
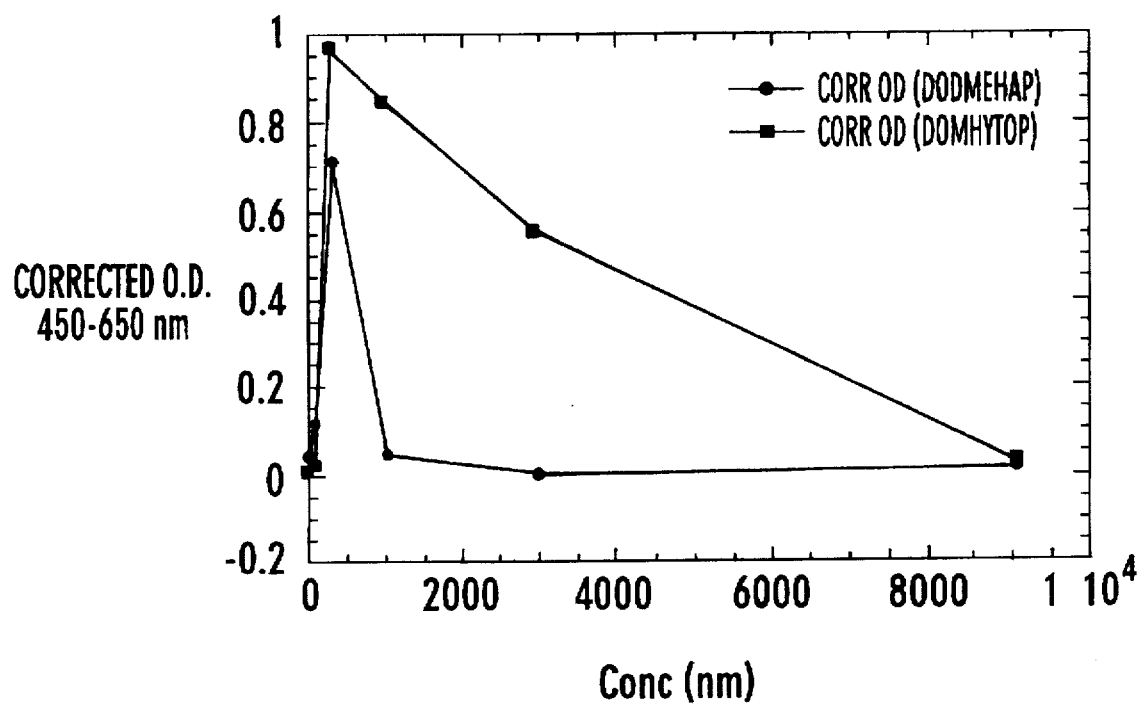
FIG. 4 illustrates the effects of liposome formulations containing either DODMEHAP or DOMHYTOP and an anti-HIV antisense oligonucleotide on cellular metabolic activity.

As depicted in FIG. 4, using increasing concentrations of liposomes prepared as described in Example III, liposomes with the ammonium ion-containing lipid (DODMEHAP) began to show signs of toxicity (as evidenced by a decrease in O.D.) at much lower concentrations than the liposomes with the equivalent sulfonium ion-containing lipid (DOMHYTOP).

Other aspects, uses and advantages of the present invention will be apparent to those skilled in the art upon review of the present disclosure. Those skilled in the art also will recognize that numerous changes can be made to the structures and methods described herein without departing from the spirit of the invention. The following claims therefore set forth the scope of the present invention, which claims are not to be limited by the specific embodiments described above in the specification.

---

We claim:

1. A composition comprising at least one optionally modified oligonucleotide conjugated to at least one thiocationic lipid of the general formula:

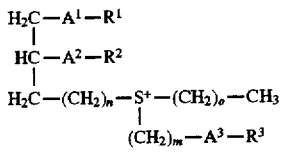

and optical isomers and/or salts thereof wherein:

$A^1$ and $A^2$ are the same or different and are —O—CO—, —O—, —S—CO— or —S—;

$A^3$ is —O—, —O—CO—, —CO—O—, —S—, —S—CO—, —CO—S, —O—CS—, —CS—O—, —CO—NH—, —NH—CO—, —CS—NH—, —NH—CS—, —NH—CO—O—, —NH—CO—NH—, —O—CO—NH—, or is absent;

$R^1$ and $R^2$ are the same or different and are H, or $C_1$ to $C_{23}$ saturated or partially saturated alkyl or aralkyl, with the proviso that at least one of $R^1$ and $R^2$ is not H;

$R^3$ is a $C_1$ to $C_{12}$ alkyl, aralkyl, alkaryl, heterocyclyl or heteroaryl; or $R^3$ is an amino acid, a dipeptide, a tripeptide, a tetrapeptide or a pentapeptide; or $R^3$ is $-[(CH_2)_p-NR^4]_q-R^4$, $-(CH_2)_p-NR^4{}_3{}^+$,

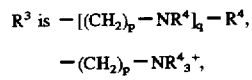

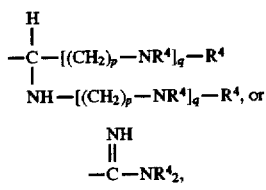

wherein p is an integer from 1 to 5, q is an integer from 0 to 4, and $R^4$ is H or a $C_1$ to $C_4$ alkyl, and each of m, n and o is an integer from 0 to 8, with the provisos that $m \geq 1$ and $(m+n+o) \geq 3$, and wherein said thiocationic lipid facilitates the entry of at least one said optionally modified oligonucleotide into a cell in vitro.

2. The composition of claim 1 wherein:

$A^1$ and $A^2$ are each independently selected from the group consisting of —O—, —O—CO—, and —S—;

$R^1$ and $R^2$ are each independently selected from the group consisting of
i) a saturated or partially unsaturated $C_2$—$C_{23}$ alkyl group,
ii) benzyl, and
iii) phenethyl;

$A^3$ is selected from the group consisting of —O—, —CO—O, —S—, and —NH—CO—, or is absent;

$R^3$ is selected from the group consisting of:
i) saturated or partially unsaturated $C_1$-$C_{12}$ alkyl or aralkyl,
ii) $_q$—$R^4$, wherein p is from 3 to 4 q is from 0 to 4 and $R^4$ is H, and
iii) —$(CH_2)_p$—$NR_3{}^{4+}$, wherein p is from 2 to 3 and $R^4$ is methyl, and iv)

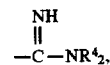

wherein $R^4$ is methyl.

3. The composition of claim 2 wherein:

$R^1$ and $R^2$ are each independently selected from the group consisting of:
i) a saturated or partially unsaturated $C_2$-$C_{23}$ alkyl group, and
ii) benzyl;

$A^3$ is —O—;

n=0-8;

o=0-8;

m=1 to 8; and $R^3$ is $_q$—$R^4$.

4. The composition of claim 3 wherein:

$R^1$ and $R^2$ are each independently selected from the group consisting of:
i) a saturated or partially unsaturated $C_{18}$ alkyl group;
ii) a saturated or partially unsaturated $C_{16}$ alkyl group; and
iii) benzyl, and m=6.

5. The composition of claim 4 wherein:

$A^1$ and $A^2$ are both —O—;

$R^1$ is a saturated $C_{16}$ or $C_{18}$ alkyl group and $R^2$ is a benzyl group;

n=0;

o=0;

q=0; and $R^4$ is H.

6. The composition of claim 2 wherein:

$R^1$ and $R^2$ are each independently selected from the group consisting of:
i) a saturated or partially unsaturated $C_2$-$C_{23}$ alkyl group, and
ii) benzyl;

$A^3$ is —CO—O;

n=0-8;

o=0-8;

m=1 to 8; and $R^3$ is $_q$—$R^4$.

7. The composition of claim 6 wherein:

$R^1$ and $R^2$ are each independently selected from the group consisting of:
i) a saturated or partially unsaturated $C_{18}$ alkyl group;
ii) a saturated or partially unsaturated $C_{16}$ alkyl group; and
iii) benzyl, and m=5.

8. The composition of claim 7 wherein:

$A^1$ and $A^2$ are both —O—;

$R^1$ is a saturated $C_{16}$ or $C_{18}$ alkyl group and $R^2$ is a benzyl group;

n=0;

o=0;

q=0; and $R^4$ is H.

9. The composition of claim 4 wherein:

$A^1$ and $A^2$ are both —O—;

$R^1$ is a saturated $C_{16}$ or $C_{18}$ alkyl group and $R^2$ is a benzyl group;

n=0;

o=0;

q=0; and $R^4$ is H.

10. The composition of claim 1 wherein said optionally modified oligonucleotide and said thiocationic lipid comprise two moieties joined by a covalent linkage, said linkage being formed by reaction of a N-hydroxysuccinate group of one of said moieties with an amino group of the other of said moieties.

11. The composition of claim 1 wherein said optionally modified oligonucleotide is a phosphorothioate oligonucleotide.

12. A method for introducing at least one optionally modified oligonucleotide into a cell in vitro, said method comprising the steps of:

a) providing a formulation comprising at least one optionally modified oligonucleotide conjugated to at least one thiocationic lipid of the general formula:

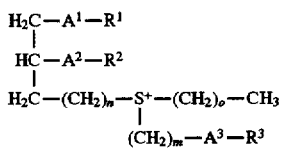

and optical isomers and/or salts thereof wherein:

$A^1$ and $A^2$ are the same or different and are —O—CO—, —O—, —S—CO— or —S—;

$A^3$ is —O—, —O—CO—, —CO—O—, —S—, —S—CO—, —CO—S—, —O—CS—, —CS—O—, —CO—NH—, —NH—CO—, —CS—NH—, —NH—CS—, —NH—CO—O—, —NH—CO—NH—, —O—CO—NH—, or is absent;

$R^1$ and $R^2$ are the same or different and are H, or $C_1$ to $C_{23}$ saturated or partially unsaturated alkyl or aralkyl, with the proviso that at least one of $R^1$ and $R^2$ is not H;

$R^3$ is a $C_1$ to $C_{12}$ alkyl, aralkyl, alkaryl, heterocyclyl or heteroaryl; or $R^3$ is an amino acid, a dipeptide, a tripeptide, a tetrapeptide or a pentapeptide; or

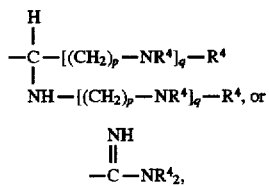

wherein p is an integer from 1 to 5, q is an integer from 0 to 4, and $R^4$ is H or a $C_1$ to $C_4$ alkyl and each of m, n and o is an integer from 0 to 8 with the provisos that m≧1 and (m+n+o)≧3, and b) contacting an animal cell with said formulation in vitro, whereby said thiocationic lipid facilitates the entry of at least one said optionally modified oligonucleotide into said cell.

13. The method of claim 12 wherein:

$A^1$ and $A^2$ are each independently selected from the group consisting of —O—, —O—CO—, and —S—;

$R^1$ and $R^2$ are each independently selected from the group consisting of:

i) a saturated or partially unsaturated $C_2$-$C_{23}$ alkyl group, ii) benzyl, and iii) phenethyl;

$A^3$ is selected from the group consisting of —O—, —CO—O—, —S—, —NH—CO—, or is absent;

$R^3$ is selected from the group consisting of:

i) a saturated or partially unsaturated $C_1$-$C_{12}$ alkyl or aralkyl, ii) 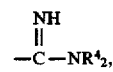—$R^4$ wherein p is from 3 to 4, q is from 0 to 4 and $R^4$ is H, iii) —$(CH_2)_p$—$NR_3^{4+}$, wherein p is from 2 to 3 and $R^4$ is methyl, and iv)

$$\begin{array}{c} NH \\ \parallel \\ -C-NR^4{}_2, \end{array}$$

wherein $R^4$ is methyl.

14. The method of claim 13 wherein:

$R^1$ and $R^2$ are each independently selected from the group consisting of;

i) a saturated or partially unsaturated $C_2$-$C_{23}$ alkyl group, and ii) benzyl;

$A^3$ is —O—;

n=0–8;

o=0–8;

m=1 to 8; and $R^3$ is $_q$—$R^4$.

15. The method of claim 14 wherein:

$R^1$ and $R^2$ are each independently selected from the group consisting of:

i) a saturated or partially unsaturated $C_{18}$ alkyl group;

ii) a saturated or partially unsaturated $C_{16}$ alkyl group, and iii) benzyl; and m=6.

16. The method of claim 15 wherein:

$A^1$ and $A^2$ are both —O—;

$R^1$ is a saturated $C_{16}$ or $C_{18}$ alkyl group and $R^2$ is a benzyl group;

n=0;

o=0;

q=0; and $R^4$ is H.

17. The method of claim 13 wherein:

$R^1$ and $R^2$ are each independently selected from the group consisting of:

i) a saturated or partially unsaturated $C_2$-$C_{23}$ alkyl group, and ii) benzyl;

$A^3$ is —CO—O;

n=0–8;

o=0–8;

m=1 to 8; and $R^3$ is $_q$—$R^4$.

18. The method of claim 17 wherein:

$R^1$ and $R^2$ are each independently selected from the group consisting of:
  i) a saturated or partially unsaturated $C_{18}$ alkyl group,
  ii) a saturated or partially unsaturated $C_{16}$ alkyl group, and
  iii) benzyl; and m=5.

19. The method of claim 18 wherein:

$A^1$ and $A^2$ are both —O—;

$R^1$ is a saturated $C_{16}$ or $C_{18}$ alkyl group and $R^2$ is a benzyl group;

n=0;
o=0;
q=0; and
$R^4$ is H.

20. The method of claim 12 wherein said optionally modified oligonucleotide is a phosphorothioate oligonucleotide.

* * * * *

UNITED STATES PATENT AND TRADEMARK OFFICE
CERTIFICATE OF CORRECTION

PATENT NO. : 5,756,352
DATED : May 26, 1998
INVENTOR(S) : SRIDHAR et al.

It is certified that error appears in the above-identified patent and that said Letters Patent is hereby corrected as shown below:

In claim 1, column 21, line 4, replace ";" with --:--.

In claim 2, column 21, line 64, before "$_q$-R$^4$" insert ---[(CH$_2$)$_p$-NR$^4$]--, and after "4" insert --,--.

In claim 3, column 22, line 19, before "$_q$-R$^4$" insert ---[(CH$_2$)$_p$-NR$^4$]--.

In claim 6, column 22, line 49, before "$_q$-R$^4$" insert ---[(CH$_2$)$_p$-NR$^4$]--.

In claim 13, column 24, line 16, before "$_q$-R$^4$" insert ---[(CH$_2$)$_p$-NR$^4$]--.

In claim 14, column 24, line 37, before "$_q$-R$^4$" insert ---[(CH$_2$)$_p$-NR$^4$]--.

In claim 17, column 24, line 66, before "$_q$-R$^4$" insert ---[(CH$_2$)$_p$-NR$^4$]--.

Signed and Sealed this

Fifteenth Day of September, 1998

Attest:

BRUCE LEHMAN

*Attesting Officer*  Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CTTCGGGCCT GTCGGGTCCC CTCGGG     26

( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CCCGAGGGGA CCCGACAGGC CCGAAG     26